United States Patent [19]

Tartaglia

[11] 4,452,106
[45] Jun. 5, 1984

[54] TOOL HAVING ARTICULATED OPPOSING JAWS

[76] Inventor: John A. Tartaglia, 108 Stoddard Rd., Waterbury, Conn. 06708

[21] Appl. No.: 341,906

[22] Filed: Jan. 22, 1982

[51] Int. Cl.³ .................... B25B 9/02; A61B 17/28; A61B 17/30
[52] U.S. Cl. ........................ 81/43; 128/354; 7/900; 294/99 R
[58] Field of Search ............ 81/43, 421, 423, 428 R; 294/99 R; 128/354, 321, 346; 7/900; D28/55

[56] References Cited

U.S. PATENT DOCUMENTS

| | | |
|---|---|---|
| 1,758,490 | 5/1930 | Aderer ........................... 81/43 |
| 2,764,905 | 10/1956 | Thoms ........................... 81/43 |
| 3,465,621 | 9/1969 | Ladd ............................. 81/43 |
| 3,653,389 | 4/1972 | Shannon ......................... 81/43 |
| 3,677,112 | 7/1972 | Keniston ......................... 81/43 |
| 3,818,784 | 6/1974 | McClure ......................... 81/43 |
| 3,977,410 | 8/1976 | Huston et al. .................... 81/43 |
| 4,212,305 | 7/1980 | Lahay ........................... 81/43 |

FOREIGN PATENT DOCUMENTS

| | | |
|---|---|---|
| 59555 | 10/1891 | Fed. Rep. of Germany ......... 81/43 |
| 561890 | 10/1932 | Fed. Rep. of Germany ......... 81/43 |
| 690823 | 4/1953 | United Kingdom ................ 81/43 |
| 1407948 | 10/1975 | United Kingdom ................ 81/43 |

Primary Examiner—Roscoe V. Parker
Attorney, Agent, or Firm—St. Onge, Steward, Johnston & Reens

[57] ABSTRACT

A tool, such as tweezers or scissors, having articulated opposing jaws is disclosed. The tool comprises a handle having first and second opposing arms projecting from a section by which the arms are joined, the arms being normally spaced throughout their length and being resiliently flexible toward each other. Each arm includes an elongate cavity extending longitudinally thereof and having an opening at the end of the arm. Jaw inserts are provided, and each has a working end for manipulating or cutting an object and an elongate shank that is received by one of the cavities to secure the jaw insert to its respective arm. The tool further includes a mechanism for guiding each working end in a single plane of movement with respect to the opposing arm upon flexing of the arms toward each other to substantially avoid undesirable lateral flexing of the opposing working ends with respect to each other.

17 Claims, 23 Drawing Figures

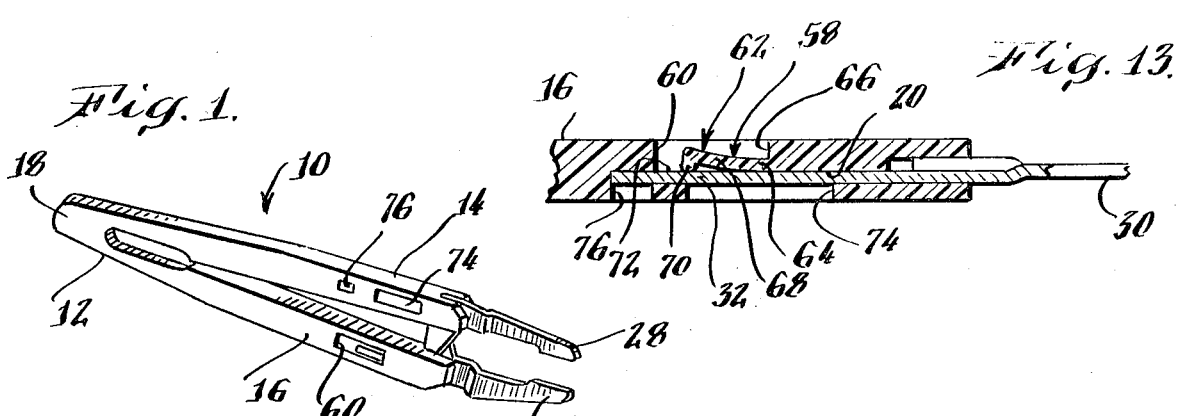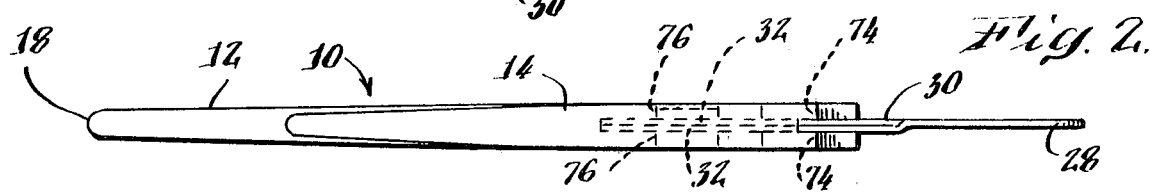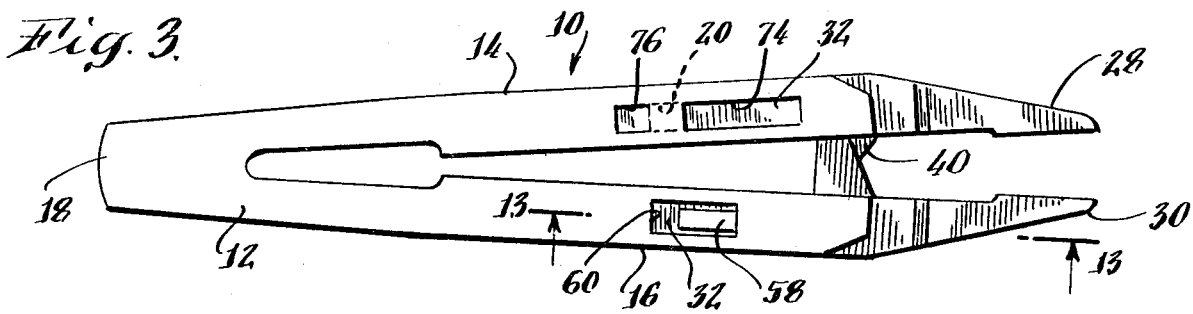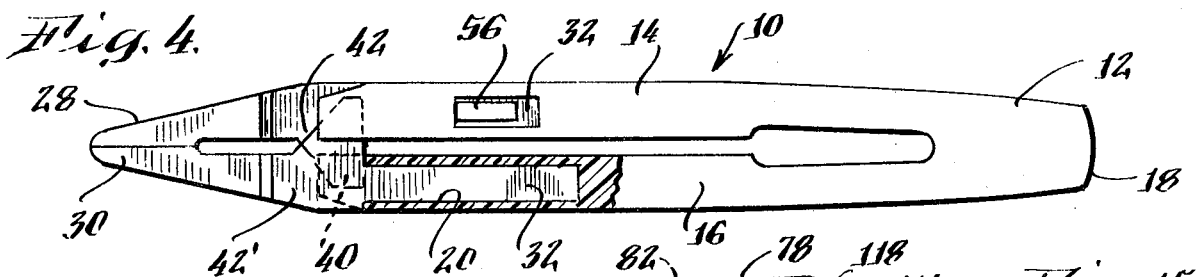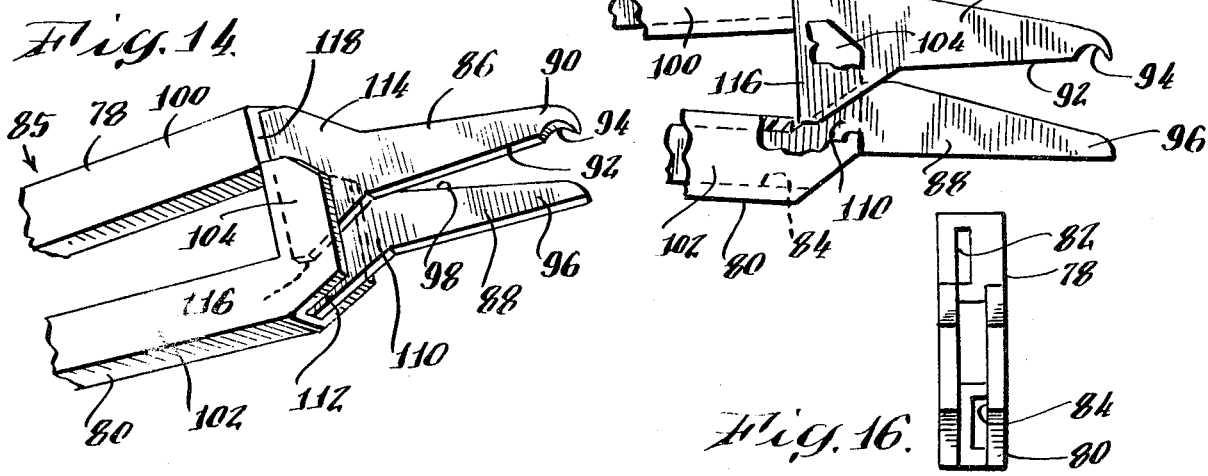

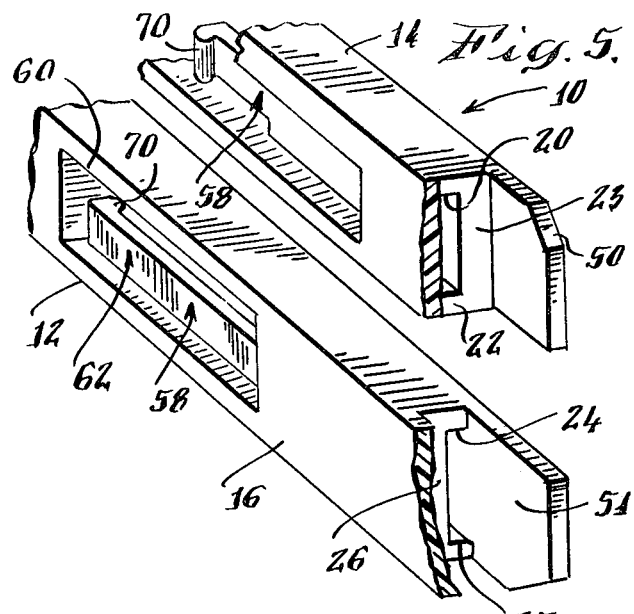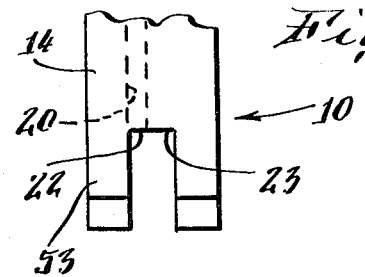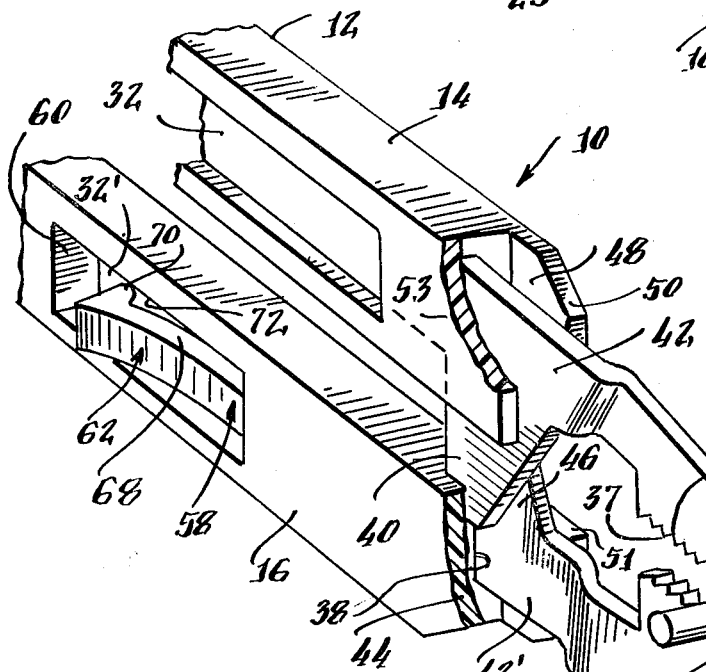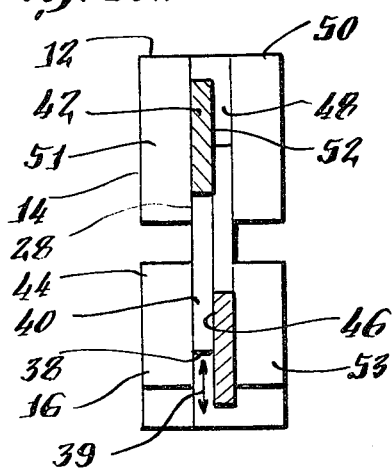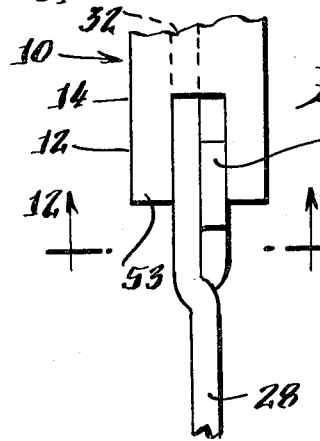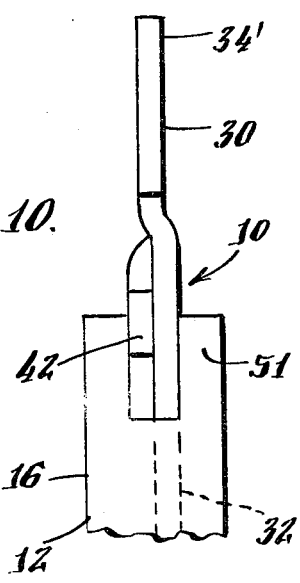

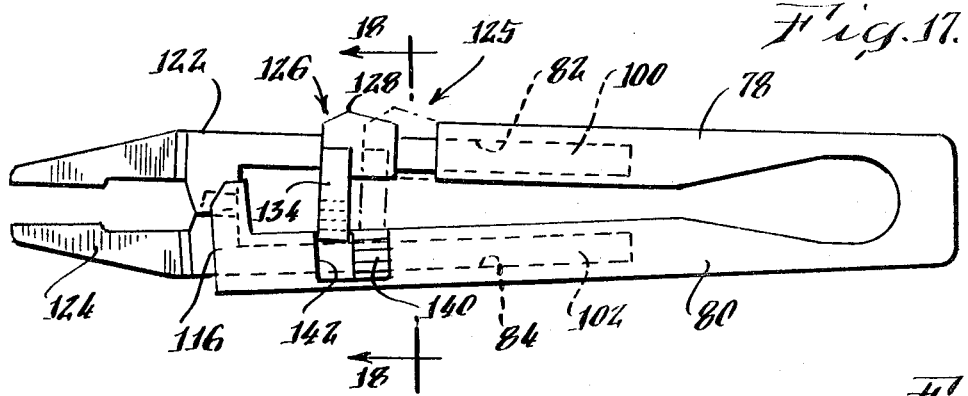
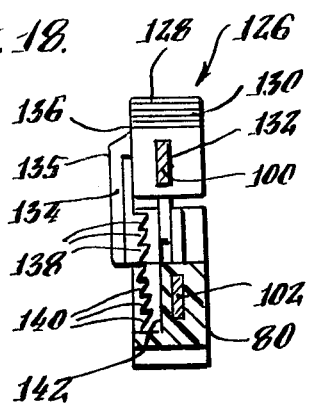
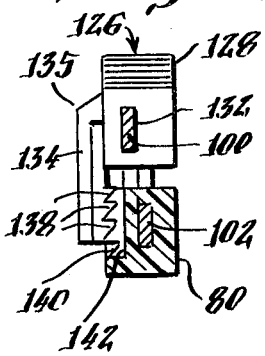
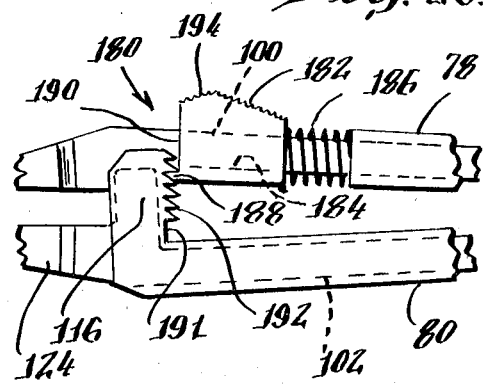
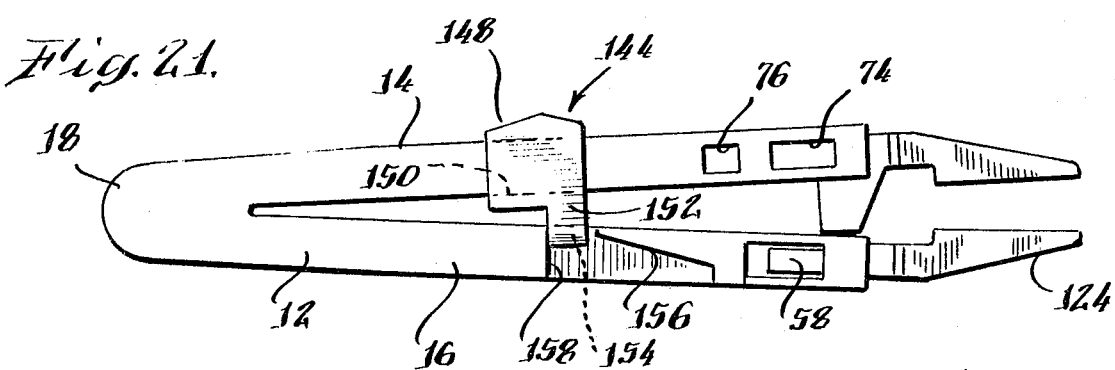
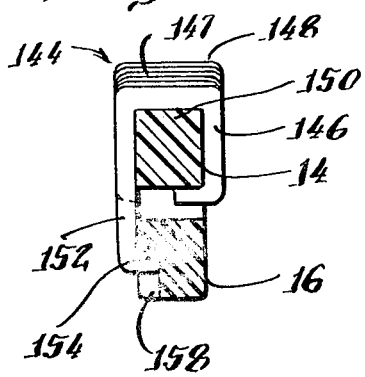
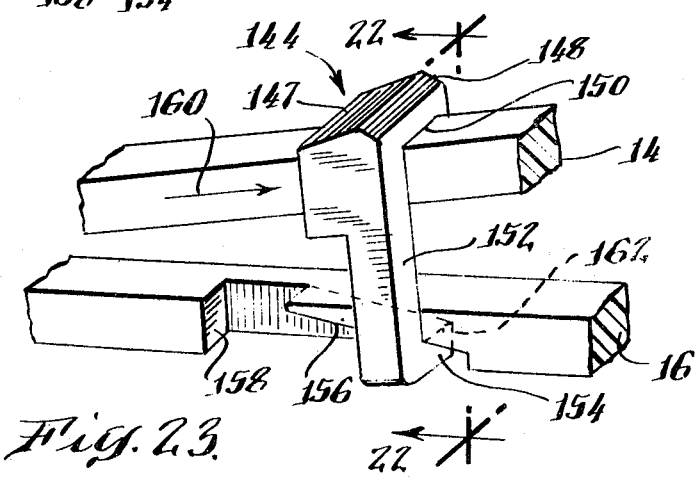

TOOL HAVING ARTICULATED OPPOSING JAWS

BACKGROUND OF THE INVENTION

1. Field of the Invention

The present invention relates to tools having articulated opposing jaws, such as, for example, forceps, hemostats and scissors, and the like. More particularly, the invention relates to such tools that are inexpensive to manufacture and that are preferably disposable.

2. Description of the Prior Art

Tools having articulated opposing jaws, that is, forceps hemostats, or scissors, are well known and are often made of metal. These tools may be used in medical, cosmetic, manufacturing and other applications. In applications such as, for example, surgery, the tools are either made of metal and can be resterilized after each use or are made of plastic so that they may be discarded. Examples of disposable medical forceps, also called "tweezers", are shown in the following U.S. Pat. Nos.: Metcalf 1,380,232; Johnson 2,082,062; Thomas 2,818,866; Whitton et al. 3,140,715; Eizenberg 3,367,336; Bean 3,648,702; Hamlon 3,392,727; Shannon 3,653,389; Chester 3,815,609; Read et al. 3,817,078; Weston 3,906,957; Huston et al. 3,977,410; Wannag 4,044,771 and Lahay 4,212,305.

Prior art tweezers made of plastic and intended to be discarded after use, have the disadvantage that the plastic material from which they are made must be sufficiently resilient and flexible to provide a spring-action movement of two opposing arms that are joined at their ends, while also, the plastic material must be sufficiently rigid in the region of the working ends of the jaws to enable positive gripping of an object. Thus, a disadvantageous trade-off often exists between providing arms that are sufficiently resilient to enable spring action movement of the arms and providing working ends that are sufficiently rigid to enable positive gripping.

Moreover, prior art disposable tools have opposing jaws that tend to flex laterally with respect to each other during use. In forceps and hemostats wherein it is desirable that the jaws move in a single plane of movement to provide positive gripping, lateral flexing may cause unwanted release of the object being grasped. In scissors, lateral flexing of the jaws may result in inability of the scissors to cut. In surgical applications, undesirable lateral flexing of the jaws may result injury to the patient.

SUMMARY OF THE INVENTION

In accordance with the present invention, a tool, such as forceps, a hemostat or scissors, having articulated opposing jaws is provided. The tool includes a handle including first and second opposing arms projecting from a section by which the arms are joined. The arms are normally spaced throughout their length and are resiliently flexible toward each other. Each arm includes an elongate cavity extending longitudinally of the arm and having an opening at the end of the arm.

A jaw insert is provided for each of the arms, each jaw insert having a working end for manipulating or cutting an object and an elongate shank received by its respective cavity to thereby secure the jaw insert to its respective arm. Depending upon the particular application in which the tool is to be used, the working ends may be formed as the ends of forceps or a hemostat, or as the blades of scissors. In a forceps application, the working ends each have a surface moveable in a single plane toward a similar surface on the opposing working end to allow an object to be grasped. In the application wherein the tool is to be used as scissors, the working ends are shaped in the form of blades and are moveable in planes offset from each other to provide a cutting action. The jaw inserts are preferably made of sheet metal material having a generally uniform thickness so that they may be formed by a simple staping operation.

In accordance with one aspect of the present invention, the tool includes a mechanism for guiding the working end of each jaw insert in a single plane of movement with respect to the opposing arm upon flexing of both arms toward each other. The guiding mechanism comprises a guide slot in one arm for receiving a tab extending inwardly from the jaw insert secured to the opposite arm. The guide slot confines movement of the tab, and thus the jaw insert, in a single plane of movement with respect to the opposing arm to thereby prevent any substantial lateral flexing which has been found to be a problem in prior art tools. In accordance with a preferred aspect of the present invention, the cavity openings in the opposing arms are offset laterally from each other to locate the shank of one jaw insert in a plane laterally offset from the shank of the other jaw insert. One of the arms includes a retaining wall extending longitudinally fowardly from the end of the arm and spaced laterally apart from a side of the jaw insert secured to that arm to define there-between the guide slot which receives the tab on the opposite jaw insert.

In accordance with another aspect of the invention, the tool includes a mechanism for the releasably securing each jaw insert in its respective cavity. The securing mechanism comprises a securement member biased laterally into the cavity for frictionally engaging the shank of its respective jaw insert. A preferred form of the securing mechanism comprises a resilient flexible tongue having one end portion fixed to the arm and a free end portion extending longitudinally of the elongate cavity, the tongue includes a protrusion on the free end portion thereof extending into the cavity. The protrusion is biased by the tongue laterally against and is frictionally engaged with a shank surface on the jaw insert positioned in the cavity.

The tool may also include a mechanism for retaining the arms in flexed position relative to each other. This retaining mechanism is particularly useful in forceps wherein it is desirable to grasp an object without maintaining finger pressure on the arms to hold them together.

BRIEF DESCRIPTION OF THE DRAWINGS

FIG. 1 is a perspective view of a tool in accordnace with the present invention;

FIG. 2 is a top plan view of the tool shown in FIG. 1;

FIG. 3 is a side plan view of one side of the tool shown in FIGS. 1 and 2;

FIG. 4 is a side plan view of a side of the tool opposite to the side shown in FIG. 3 with a portion of the handle broken away to expose a jaw insert;

FIG. 5 is a perspective view of the tool shown in FIGS. 1-5 with jaw inserts removed;

FIG. 6 is a top plan view of the tool handle shown in FIG. 5;

FIG. 7 is a bottom plan view of the tool handle shown in FIG. 5;

FIG. 8 is a front plan view of the tool handle shown in FIG. 7;

FIG. 9 is a perspective view of the tool shown in FIG. 5 with the jaw inserts in place;

FIG. 10 is a top plan view of the tool shown in FIG. 9;

FIG. 11 is a bottom plan view of the tool shown in FIG. 9;

FIG. 12 is a front plan view of the tool shown in FIG. 9 with the front portion of the jaw inserts sectioned away;

FIG. 13 is a section view along the plane 13—13 of FIG. 3;

FIG. 14 is a bottom and side perspective view of another embodiment of tool in accordance with the present invention wherein the tool is a pair of suturing scissors;

FIG. 15 is a side view of the tool shown in FIG. 14;

FIG. 16 is a front plan view of the tool shown in FIGS. 14 and 15, but with the jaw inserts of the tool removed;

FIG. 17 is a side view of another embodiment of tool with accordance of present inventions;

FIG. 18 is a sectional view along the plane 18—18 of FIG. 17;

FIG. 19 is a view similar to that of FIG. 18 except that the arms of the tool have been flexed together;

FIG. 20 is a side view of another embodiment of a tool in accordance with the present invention;

FIG. 21 is a side view of another embodiment of a tool in accordance with the present invention;

FIG. 22 is a sectional view along the plane 22—22 of FIG. 21; and

FIG. 23 is a perspective view of a portion of the tool shown in FIGS. 21 and 22.

DETAILED DESCRIPTION OF THE PREFERRED EMBODIMENTS OF THE INVENTION

Referring to FIGS. 1 through 13, one embodiment of a tool having articulated opposing jaws in accordance with the present invention is shown. In the embodiment shown in these figures, the tool comprises forceps, also referred to as "tweezers." Tool 10 comprises a handle 12 having a first arm 14 and a second arm 16. The arms 14 and 16 are normally spaced throughout their length and are resiliently flexible toward each other when they are grasped by hand and urged together. Preferably, the handle is molded in a single piece from plastic. Various types of resilient flexible plastics may be used.

Referring in particular to FIGS. 4 through 8, arm 14 includes an elongate cavity 20 extending longitudinally of arm 14 and having an opening 22 at the end 23 of the arm. Cavity 20 preferably has a rectangular cross-sectional shape. Similarly, arm 16 includes an elongate cavity 24 extending longitudinally of arm 16 and having an opening 25 on the end 26 of the arm. The cavity openings 22 and 25 in opposing arms 14 and 16 respectively are offset laterally from each other so that, as will be described hereinafter, the shanks of jaw inserts positioned therein will be located in a planes laterally offset from each other.

Referring in particular to FIG. 9, as well as FIGS. 3, 4 and 13, the tool includes a first jaw insert 28 and a second jaw insert 30. In the embodiment of the invention shown in FIGS. 1 through 13, jaw inserts 28 and 30 are substantially identical so that like reference numerals will be applied to both jaw inserts except that the numerals for the lower jaw insert 30 will be followed with a (') prime. The jaw inserts 28 and 30 include respectively shanks 32 and 32' that are sized and shaped to be tightly received respectively by cavities 20 and 24. Each jaw insert also includes a working end 34 and 34', which in the case of the forceps shown in FIGS. 1 through 13, has a surface 36 and 36', having a plurality of teeth 37 and 37' thereon which mesh with teeth on the opposite jaw insert. The jaw inserts are formed of sheet material having a generally uniformed thickness and, preferably are formed from sheet steel in a stamping operation. The stamping operation enables the jaw inserts to be produced inexpensively in large numbers.

A tool in accordance with one aspect of the invention includes a mechanism for guiding the working end of one jaw insert in a single plane of movement with respect to the opposing arm upon flexing to the arms toward each other to substantially avoid undesirable lateral flexing of the working ends of the jaw inserts. More particularly, as shown in FIG. 9, the guiding mechanism which will be described immediately below, guides working end 34 in a single plane of movement with respect to working end 34' to substantially avoid undesirable lateral flexing of the working ends with respect to each other. As shown in FIG. 9, if working ends 34 and 34' move laterally with respect to each other, object 35 that is being grasped between the working ends may be accidentally released. The guiding mechanism comprises a slot 38 (see FIGS. 9 and 12) in arm 16 that receives a tab 40 protruding inwardly into the space between the arms from an intermediate portion 42 of the jaw insert 34. The intermediate portion 42 is located intermediate the working end 34 and the shank 32 and is coplanar with shank 32. As best shown in FIGS. 9 and 12, the guide slot 38 receives tab 40 and confines movement of the working end 34 of the first jaw insert 28 in a generally planar relation to the second jaw insert as shown by arrow 39 in FIG. 12.

Arm 16 includes a retaining wall 44 (see FIGS. 5, 7, 8, 9 and 12), which extends longitudinally forwardly from the end 26 to the arm 16 and is spaced laterally apart from a side 46 (see FIGS. 9 and 12) of the intermediate portion 42' on the opposite jaw insert to define therebetween guide slot 38. As can well be appreciated, for purposes of substantially preventing lateral flexing of the working ends 34 and 34' with respect to each other, it is necessary to have only one guide slot 38 which receives a tab 40 in the opposing jaw insert. However, in the embodiment shown in FIGS. 1 through 13, a guide slot is provided on each arm for receiving a tab protruding inwardly from the jaw insert secured to the opposing arm. More particularly, a guide slot 48 (see FIGS. 9 and 12) is provided in arm 14. Arm 14 includes a retaining wall 50 extending longitudinally from the end 23 of the arm 14 and spaced laterally apart from a side 52 (see FIG. 12) on intermediate portion 42 of jaw insert 28 to define therebetween the guide slot 48. Each arm optionally includes retaining walls 51 and 53 that extend respectively in spaced and parallel reation to retaining walls 44 and 50. Walls 51 and 53 substantially prevent intermediate portion 42' and 42 from flexing laterally outwardly.

As described earlier, the cavity opening 22 in arm 14 is laterally offset from the cavity opening 24 in arm 15 so that jaw inserts 28 and 30 have their respective shanks 32 and 32' and intermediate portions 42 and 42' disposed in planes offset from each other. In the case of the forceps shown in FIG. 9, for each jaw insert, the working end 34 and 34' is located in a plane parallel to and offset from a plane in which the respective intermediate portion 42 and 42' and the shank 32 and 32' are disposed. The lateral offset for the working end of each jaw insert is preferably one half of the thickness of each jaw insert to thereby provide opposing working ends that are movable in co-planar relation to each other. Thus, in a forceps application, the working ends 34 have surfaces 36 and 36' that are movable in a single plane toward each other to enable object 35 to be grasped. It should be understood, however, that the jaw inserts shown in FIG. 9 may be replaced with other jaw inserts to provide scissors or other tools having opposing jaws. In an application for scissors, each jaw insert has a working end that extends in planar relation to its shank and intermediate portion to provide a cutting action wherein the working ends of opposing jaw inserts move in planes laterally offset with respect to each other provide a cutting action as will be apparent from the embodiment of the tool described hereinafter with respect to FIGS. 14, 15 and 16.

Referring to particularly FIGS. 5, 9 and 13 as well as FIG. 1 through 4, a mechanism for releasably securing each jaw insert in its respective cavity will now be described. Arm 14 includes securement mechanism 56 while arm 16 includes securement mechanism 58. Both securement mechanisms 56 and 58 are identical in construction and therefore, only securement mechanism 58 will be described in detail.

Each arm includes an elongate aperture 60 extending into its respective cavity. A resilient flexible tongue 62 has one end portion fixed to a wall 66 (see FIG. 13) and includes a free end portion 68 extending lengthwise in the elongate aperture 60. The free end portion 68 includes at the end thereof a protrusion 70 that extends into the cavity. The protrusion 70 is biased by the tongue 62 laterally into the cavity. The protrusion 70 is preferably rounded so that a shank portion inserted into the cavity will contact the rounded protrusion and urge it, as well as the tongue 62, laterally outwardly as the shank is inserted. As shown particularly well in FIGS. 9 and 13, the protrusion 70 is biased by the tongue 62 laterally against and is frictionally engages a shank surface 72 of the jaw insert positioned in the cavity.

Referring in particular to FIG. 13, in addition to aperture 60, arm 16 includes apertures 74 and 76 which extend into the cavity 20 from a side of the arm opposite to the side from which aperture 60 extends. Apertures 76 and 74, which are offset laterally from aperture 60, allow for ease of molding of an arm having a cavity that is relatively deep and that has at one side thereof a tongue 62. It should be understood that securement mechanism 58 is adaptable to any device or tool or wherein it is desirable to secure a jaw insert to an elongate arm, and thus, the securement mechanism 58 could be used in conventional scissors of the type having two handles wherein each handle includes a cavity receiving a blade insert.

Referring to FIGS. 14 through 16, another embodiment of a tool having articulated opposing jaws in accordance with the present invention is shown. In the embodiment shown in these figures, the tool comprises suturing scissors. The scissors include opposing arms 78 and 80 which are joined in a manner similar to the tool described with respect to FIGS. 1 ghrough 13. Referring in particular to FIGS. 15 and 16, arms 78 and 80 include respectively elongate cavities 82 and 84 that extend longitudinally with respect to arms 78 and 80. As shown particularly well in FIG. 16, cavities 82 and 84 are located in planes offset from each other. Jaw inserts 86 and 88 are provided. Jaw insert 86 includes a working end 90 having a cutting blade 92 and recess 94 for grasping and cutting a suture. It should be understood that blade 92 may be formed by surfaces intersecting at a right angle as shown in FIG. 14, or, as is typically done in the manufacture of conventional scissors, the blade may be sharpened to form a beveled edge. Jaw insert 88 includes a working end 96 having a cutting edge 98.

Jaw insert 86 includes a shank 100 sized and shaped to be received snugly by cavity 82 and jaw insert 88 includes a shank 102 sized and shaped to be received snugly by cavity 84. Arm 80 includes a retaining wall 104 extending longitudinally forwardly and inwardly from the end 106 of arm 80. Retaining wall 104 has an interior surface 108 that is spaced laterally from the surface 110 on the jaw insert 88 to define a guide slot 112 between surface 110 and surface 108 (see FIG. 14). As can be best seen in FIG. 14, jaw insert 86 includes an intermediate portion 114 having a tab 116 that extends into guide slot 112. The guide slot 112 confines movement of the tab 116 in a single plane. Guide slot 112 guides working end 90 of jaw insert 86 in a single plane of movement with respect to arm 80. Optionally, a second retaining wall 116 extends longitudinally forwardly and inwardly from end 106 of arm 80 and is located immediately adjacent cavity 84. Retaining wall 116 aids in preventing lateral flexing of the intermediate portion of jaw insert 88.

As can be well appreciated, the scissors shown in FIGS. 14 through 16 may include a mechanism for securing each jaw insert shank in its respective cavity, and, more particularly, the securing mechanism can be of the type described above and shown in FIG. 13 at reference character 58.

As shown in FIG. 14, the end 118 of arm 78 is spaced just slightly rearwardly of the retaining walls 104 and 116 to allow these walls to move past 118 when the arms of the tool are flexed toward each other.

The tool shown in FIGS. 14 through 15 may be adapted to receive jaw inserts that provide forceps, rather than inserts 86 and 88 that provide scissors as shown in FIGS. 14 through 16. More particularly, jaw inserts 78 and 80 may be replaced with jaw inserts of the type to provide tweezers, rather than scissors, such as jaw inserts 28 as shown in FIGS. 1 through 13.

Referring to FIGS. 17 through 19, another embodiment of a tool in accordance with the present invention is shown. The tool shown in these figures is a pair of forceps. The handle 120 of the tool is identical in construction to the handle 85 of the tool shown in FIGS. 14 through 16, with the exception that arm 78 has been shortened to accommodate a mechanism 125 for retaining the arms in flexed position relative to each other. Like reference characters are applied to parts of the tool shown in FIGS. 17 through 19 that correspond to the parts of the tool shown in FIGS. 14 through 16. Jaw inserts 122 and 124 are identical to jaw inserts 28 and 30 which are used in the tool shown in FIGS. 1 through 13.

FIG. 18 shows the tool prior to the arms being flexed while FIG. 19 shows the tool after the arms have been flexed. FIG. 17 shows in phantom slide 126 in a postiion wherein opposing sets of teeth 138 and 140 on opposite arms are in alignment and are about to be engaged. FIG. 17 also shows, in solid lines, slide 126 in a position wherein the opposing sets of teeth on the arms have been disengaged.

Slide 126 includes an upper surface 128 having a series of grooves and ridges 130 thereon to allow for gripping by a thumb of a person operating the tool. The slide includes a longitudinal aperture 132 which is sized and shaped to slidably receive shank 100 of jaw insert 122. Thus, slide 126 is mounted for sliding movement with respect to the first arm 78, and may be either mounted on the shank 100 as shown in FIG. 17 or directly on arm 78. Slide 126 includes a resilient, flexible element 134 having one end 135 secured to side 136 of the slide 126 and having the other end portion extending inwardly from arm 78 toward arm 80. Element 134 includes a set of teeth 138 extending along a side thereof. Another set of teeth 140 located on arm 80 are in interfering relation with teeth 138. Thus, when arms 78 and 80 are flexed together, the first set of teeth 138 rides over the second set of teeth 140. By comparing FIGS. 18 and 19 it may be seen that teeth 138 have ridden over teeth 140 and the sets of teeth are engaged with each other to lock the flexed arms 78 and 80 in any desired incremental position with respect to each other. To disengage the sets of teeth, the slide is moved forwardly to the postion shown in solid lines in FIG. 17.

Referring to FIG. 20, another tool in accordance with the invention is shown and is identical to the tool shown in FIGS. 17 through 19 with the exception that it includes another embodiment of a mechanism for retaining the arms in flexed position relative to each other. Thus, only the middle portion of the tool that includes the retaining mechanism is shown. Retaining mechanism 180 comprises a slide 182 movable in slideable relation to arm 78. Slide 182 includes a channel 184 extending therethrough that receives jaw insert 100. A spring mechanism 186, which may be a conventional coil spring, biases slide 182 forwardly so that a tooth 188 on the front end 190 thereof is urged into engagement with a vertically disposed set of teeth 192 on the rear surface 191 of retaining wall 116 and with a similar set of teeth on the rear surface of the other retaining wall (not shown in the drawings). Slide 182 includes on the upper surface thereof a series of grooves and ridges 194 for gripping by a thumb of a person operating the tool.

To operate the retaining mechanism 180, the slide is drawn rearwardly against the bias of spring 186 from the position shown in FIG. 20 to disengage tooth 188 from teeth 192. The arms 78 and 80 are then flexed toward each other to a desired position and then slide 182 is released and allowed to move forward to engage tooth 188 with teeth 192 thereby retaining arms 78 and 80 in the desired flexed position.

Referring to FIGS. 21, 22 and 23 another tool in accordance with the present invention is shown. The tool shown is identical to the tool shown in FIGS. 1 through 13 with the exception that it includes another embodiment of a mechanism for retaining the arms in flexed position relative to each other. Referring to FIGS. 21 through 23, the retaining mechanism 144 includes a slide 146 having an upper surface 148 having a series of grooves and ridges 147 thereon to allow for gripping by a thumb of a person oerating the tool. Slide 146 has an opening 150 in the body thereof sized and shaped to receive arm 14 and is slidable longitudinally with respect to arm 14. Slide 146 also includes a cam arm 152 extending from the body of slide 146 to arm 15. Cam arm 142 includes on the end thereof a cam 154 extending laterally inwardly from arm 152 and engaging cam surface 156 on the opposite arm 16. As shown particularly well in FIG. 23, cam surface 156 is preferably formed by a recess 158 in arm 16 and is sloped longitudinally forwardly and outwardly. Recess 158 includes an opening 160 at the top thereof for receiving cam arm 152.

When the slide 146 is moved forwardly from the position shown in FIG. 21 in the direction of arrow 160 to the position shown in FIGS. 22, 23 the front edge 162 of cam 154 contacts and rides along cam surface 156 to flex the arms 14 and 16 toward each other. Once the desired amount of flexing has occurred, the thumb pressure urging slide 146 forwardly may be released and the friction between front edge 162 of the cam and cam surface 156 will retain the slide in place, which in turn, retains the arms 14 and 16 in any desired flexed condition.

In summary, the above described tool of the present invention is particularly simple to manufacture in that the handle is formed of molded plastic and the jaw inserts are stamped from sheet material. The tool is versatile in that various types of jaw inserts may be used with a standard handle to form scissors, tweezers a hemostat or other tools having articulated opposing jaws.

It is understood that although specific embodiments of the invention have been described herein in detail, such description is for purposes of illustraticn only and modifications may be made thereto by those skilled in the art within the scope of the invention.

What is claimed is:

1. A tool having articulated opposing jaws comprising:
    first and second opposing arms projecting from a section by which said arms are joined, said arms being normally spaced throughout their length and being resiliently flexible toward each other, each said arm including an elongate cavity extending longitudinally of said arm and having an opening at the end of said arm;
    first and second jaw inserts respectively for said first and second arms, each jaw insert having a working end and an elongate shank received by its respective cavity, each said jaw insert being formed of sheet material of generally uniform thickness, said working ends being movable toward each other upon flexing of said arms toward each other; said first jaw insert including a portion intermediate said working end and said shank, said intermediate portion including a tab protruding inwardly there from into the space between said arms; and said second arm including a guide slot receiving the tab on the first jaw insert and confining movement of said first jaw insert in generally planar relation to said second arm.

2. A tool according to claim 1 wherein said tool comprises a tweezer and wherein
    said second jaw insert includes a portion intermediate said working end and said shank, a tab protruding inwardly therefrom into the space between the arms;
    for each said jaw insert, said working end being located in a plane parallel to and laterally offset from a plane in which said intermediate portion and shank are disposed;
    said cavity openings in said opposing arms being offset laterally from each other to locate said intermediate portion and shank of each said jaw insert in planes laterally offset from the intermediation portion and shank of the opposite jaw insert and to locate said working ends in a single plane;

said second arm end including a retaining wall extending longitudinally and inwardly from the end of said arm and spaced laterally apart from a side of the tab on said second jaw insert to define therebetween said guide slot slidably receiving the tab on said first jaw insert to thereby confine movement of said working ends in a single plane.

3. A tool according to claim 1 wherein said guiding means comprises:

each said jaw insert including a portion intermediate said working end and said end portion received by the cavity, each said intermediate portion including a tab protruding inwardly therefrom into the space between said arms; and each said arm including a guide slot receiving the tab on the opposing jaw insert and confining movement of said first and second jaw inserts in generally planar relation respectively to said second and first arms.

4. A tool according to claim 3 wherein each said arm includes a retaining wall protruding from said arm end and spaced laterally apart from a side of said jaw insert positioned in said cavity to provide said guide slot therebetween.

5. A tool according to claim 3 wherein for each said jaw insert, said working end being located in a plane parallel to and offset from a plane in which said intermediate portion and said shank are disposed; and wherein the cavity openings in said opposing arms are offset laterally from each other to locate said intermediate and said shank portion of each jaw insert in planes offset from each other and to locate said working ends in a single plane.

6. A tool according to claim 1 and further including means for releasably securing each said jaw insert in its respective cavity.

7. A tool according to claim 6 wherein each said cavity includes a securement member biased laterally into said cavity for frictionally engaging the shank of its respective jaw insert.

8. A tool according to claim 7 wherein for each said arm, said securement member comprising a resilient flexible tongue having one end portion fixed to said arm and a free end portion extending longitudinally of said elongate cavity, said tongue including a protrusion on the free end portion thereof extending into said cavity, said protrusion being biased by said tongue laterally against and being frictionally engaged with a shank surface on said jaw insert positioned in said cavity.

9. A tool according to claim 8 wherein each said arm includes an elongate aperture extending into said cavity, said tongue end portion being secured to a wall of said aperture and said free end portion extending lengthwise in the elongate aperture, said protrusion comprising a ridge rounded at the top thereof to provide ease of insertion of the jaw insert end portion into the cavity.

10. A tool according to claims 1 or 3 and further including means for retaining said arms in flexed position relative to each other.

11. A tool according to claim 10 wherein said retaining means comprises:

a slide mounted for sliding movement with respect to said first arm and having a resilient flexible element extending inwardly from said first arm toward said second arm and having one set of teeth extending along a side thereof, said second arm including another set of teeth, both said sets of teeth being aligned in normally interfering relation, said one set of teeth riding over said other set of teeth as said arms are flexed together, said sets of teeth engaging each other to lock said flexed arms in any desired incremental position with respect to each other, said slide being slidable longitudinally to disengage said sets of teeth thereby allowing the arms to flex away from each other.

12. A tool according to claim 10 wherein said retaining means comprises:

a slide mounted for sliding movement with respect to said first arm, said second arm including a set of vertically disposed teeth, said slide including at least one tooth for engaging said teeth, and further including means biasing said slide forwardly to engage said tooth with said teeth to retain said arms in flexed position, said slide being movable rearwardly to disengage said tooth from said teeth to allow said arms to flex.

13. A tool according to claim 10 wherein said retaining means comprises a sloped cam surface on one of said arms extending longitudinally forwardly and outwardly of said arm and a slide on the other arm and mounted for longitudinal sliding movement with respect to the other arm and including a cam engaging said cam surface thereby flexing said arms toward each other upon movement of said slide in one direction and retaining said arms in position with respect to each other.

14. A tool according to claims 2 or 5 wherein said offset cavities each have a rectangular cross-sectional shape, each cavity having an inner surface extending substantially coplanar in relation to the inner surface of the other cavity so that said intermediate portions of said jaw inserts positioined in said cavities have inner surfaces that abut and slide with respect to each other.

15. A tool according to claim 14 wherein said working ends of each said jaw insert are laterally offset from their respective intermediate portions by a distance of one half said jaw insert thickness to provide working ends movable in coplanar relation to each other.

16. A tool having articulated opposing jaws comprising at least one arm having an elongate cavity extending longitudinally of said arm and having an opening at the end of said arm, a jaw insert having a working end and an elongate shank received by said cavity, a securement member biased laterally into said cavity for frictionally engaging the shank of its respective jaw insert, said securement member comprising a resilient flexible tongue having one end portion fixed to said arm and a free end portion extending longitudinally of said elongate cavity, said tongue including a protrusion on a free end portion thereof extending into said cavity, said protrusion being biased by said tongue laterally against and being frictionally engaged with a shank surface on said jaw insert positioned in said cavity.

17. A tool according to claim 16 wherein said arm includes an elongate aperture extending into said cavity, said tongue end portion being secured to a wall of said aperture and said free end portion extending lengthwise in the elongate aperture, said protrusion comprising a ridge rounded at the top thereof to provide ease of insertion of the jaw insert end portion into the cavity.

* * * * *